United States Patent [19]

Maerfeld et al.

[11] Patent Number: 4,870,972

[45] Date of Patent: Oct. 3, 1989

[54] MULTIPLE-FREQUENCY ACOUSTIC TRANSDUCER, ESPECIALLY FOR MEDICAL IMAGING

[75] Inventors: Charles Maerfeld, Antibes; Jean F. Gelly, Valbonne, both of France

[73] Assignee: Thomson-CSF, Paris, France

[21] Appl. No.: 169,272

[22] Filed: Mar. 17, 1988

[30] Foreign Application Priority Data

Mar. 19, 1987 [FR] France ................................ 87 03839

[51] Int. Cl.[4] ................................................ A61B 8/00

[52] U.S. Cl. .......................... 128/662.03; 128/662.04; 310/336

[58] Field of Search ...................... 128/662.03, 662.04, 128/660.05; 73/642, 644; 310/334–337

[56] References Cited

U.S. PATENT DOCUMENTS 4,276,491 6/1981 Daniel ........................ 128/662.04 X
4,490,640 12/1984 Honda ................................ 310/325
4,503,861 3/1985 Entrekin ......................... 128/662.04

FOREIGN PATENT DOCUMENTS 3008553 9/1980 Fed. Rep. of Germany .

*Primary Examiner*—Francis Jaworski
*Attorney, Agent, or Firm*—Oblon, Spivak, McClelland, Maier & Neustadt

[57] ABSTRACT

Disclosed is a probe for medical echography wherein, between the piezoelectric transducers and the backing, there is inserted a half-wave strip at the natural resonance frequency of these transducers, thus enabling the use of the probe in two distinct frequencies, one of which is substantially equal to half the other, and thus providing for ordinary mode B imaging and DFM Doppler imaging with one and the same probe.

7 Claims, 1 Drawing Sheet

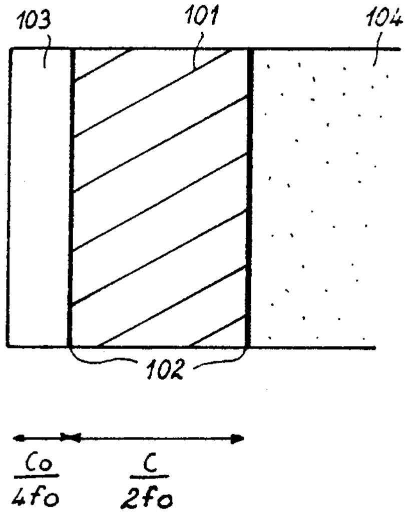
FIG_1 PRIOR ART
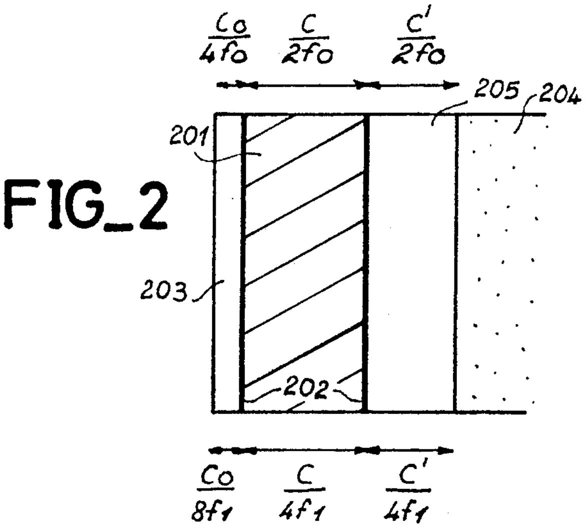
FIG_2
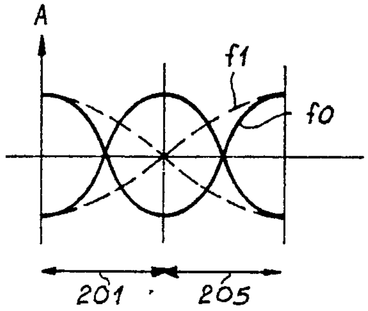
FIG_3
FIG_4
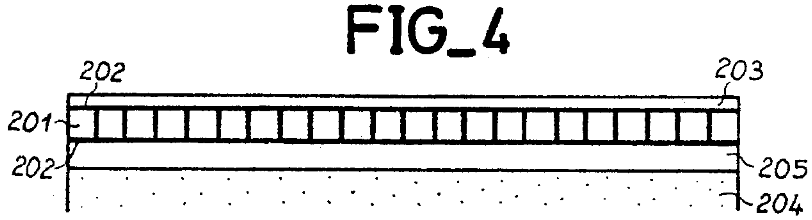

MULTIPLE-FREQUENCY ACOUSTIC TRANSDUCER, ESPECIALLY FOR MEDICAL IMAGING

BACKGROUND OF THE INVENTION

1. Field of the Invention

The present invention relates to multiple frequency acoustic transducers used, especially, in medicine to form images of the human body by echography.

2. Description of the Prior Art

Prior art methods in medical echography include the use of probes. A cross-section of a probe is shown in FIG. 1. This probe is made up of aligned transducer elements 101, the thickness of which is adapted to the operating frequency. The two sides of these elements are lined with electrodes 102 used to apply the electrical voltages which make them vibrate. The vibration frequency chosen is most usually the resonance frequency $F_r$ corresponding to the fundamental vibration mode depending on the thickness of the transducer. For the piezoelectric materials generally used in these probes, the relationship between $f_r$, expressed in kilohertz, and the thickness h, expressed in millimeters, is given by $f_r=2850/h$. Usually, for medical probes, a thickness of 1 mm is used, and the frequency used is then most often 2.85 MHz.

The Q factor of the transducers is approximately equal to the ratio between the impedance of the piezoelectric material forming this transducer and the impedance of the external medium in which the vibration will be propagated. If $\rho$ and $\rho_o$ are the relative densities of the piezoelectric material and the external environment respectively, and if c and $c_o$ are the speeds of sound in this material and in this medium respectively, then Q is equal to $\rho_c/(\rho_o c_o)$. In the case of a piezoelectric ceramic, such as the PZT, this ratio is close to 17.

The vibrations are emitted in the form of brief pulses in order to obtain adequate definition in distance. This widens the frequency band of the signal emitted and therefore makes it necessary to have a relatively large band width for the probe. To obtain this, a strip 103 is placed in front of the transducers, the thickness of this strip being a quarter of the wavelength at the fundamental frequency. The impedance of this quarter wave-strip is chosen to be in the range of $\sqrt{\rho c \rho_o c_o}$.

The transducers are fixed to the frame of the probe by means of a backing 104 which is advantageously of the soft type, i.e. with an acoustical impedance in the region of 0.

Two types of operation are habitually used in medical imaging:

standard imaging, called mode B imaging, where the echos are represented sectorially according to the aiming angle and distance, the amplitude of these echos modulating the brilliance of the image:

color-encoded imaging also called "Doppler flow mapping" or DFM where the Doppler shift due to blood circulation is represented by variations in color, in addition to variations in brilliance due to the amplitude of the echos.

For imaging in mode B, a high degree of lateral and distance definition is needed. This calls for a relatively high center frequency, for example, in the range of 5 MHz.

For DFM imaging, there is no need for definition as high as for mode B imaging, but the highest possible signal-to-noise ratio is needed to make it possible to measure small Doppler shifts themselves corresponding to low blood flow speeds. The signal-to-noise ratio is all the greater as the operating frequency is low. A typical value of the frequency used will be, for example, 2.5 MHz.

In the prior art, two probes connected to one and the same instrument are used, but this obviously increases the cost of the equipment and complicates its use. Another far less satisfactory method lies in the use of a single probe working at an intermediate frequency of 3.5 MHz for example.

SUMMARY OF THE INVENTION

To remove these disadvantages, the invention proposes to modify traditional probes by adding on further adaptation strips so that these probes can be made to work simultaneously on several frequencies and so that mode B imaging and DFM imaging can be done simultaneously with a single probe.

BRIEF DESCRIPTION OF THE DRAWINGS

Various other objects, features and attendant advantages of the present invention will be more fully appreciated as the same becomes better understood from the following detained description when considered in connection with the accompanying drawings in which like reference characters designate like or corresponding parts throughout the several views and wherein:

FIG. 1 shows a cross-section of a prior art probe;

FIG. 2 shows a cross-section of a probe according to the invention;

FIG. 3 shows an operation graph; and FIG. 4 shows a longitudinal section of a probe according to the invention.

DESCRIPTION OF A PREFERRED EMBODIMENT

In the dual frequency embodiment, shown in FIG. 2 in the same sectional view as in FIG. 1, the probe of the invention has a transducer 201 provided with two electrodes 202 and a quarter-wave strip 203. According to the invention, this transducer is fixed to the soft backing 204 by means of a half-wave strip 205.

According to the invention, this probe works at two pass bands, one centered on a high frequency $f_o$ and the other centered on a low frequency $f_1$ equal to $f_o/2$. These frequencies are, for example, equal to those mentioned above, i.e. 5 MHz and 2.5 MHz.

The terms "half wave" and "quarter wave", used respectively for the transducer 201 and the strip 205 on the one hand, and the strip 203 on the other, correspond to the high frequency. This means that since the materials used are not dispersive at the low frequency, the transducer 201 and the strip 205 are quarter-wave elements, while the strip 203 is ⅛th of the wavelength.

If the transducer were to be alone as shown in FIG. 1, it would obviously not resonate at the frequency $f_1$, and any sound signal emitted would be extremely weak.

The presence of the strip 205 does not change the frequency $f_o$ because, being a half-wave strip at this frequency, it is transparent to the sound waves and brings the same impedance as that of the backing 204 to the transducer.

By contrast, at the frequency $f_1$, since this strip is then a quarter-wave element, it is as if the transducer were to be extended by a quarter wavelength and as if the unit comprising the transducer 201 and the strip 205 were to be equivalent to a half-wave element. Thus the excitation provided by the electrodes 202 makes this set vibrate at the resonance of the frequency $f_1$.

To provide a better explanation of these phenomena, we could make a rough comparison with electromagnetism and consider the strip 205 to be a quarter-wave line or half-wave line as the case may be. This comparison is explained in FIG. 3 which represents the amplitude A of the vibrational speed along the transducer 201 and the strip 205.

A line of this type would be short-circuited at the end of the backing side where there will therefore always be a maximum vibrational speed (known as the antinode) whatever the frequency, especially at the frequencies $f_o$ and $f_1$.

At the frequency $f_o$, since the line is a half-wave line, it brings to its other end, namely, to the transducer, an impedance equal to that of the backing, namely 0 in this case. Thus, in this case, there is a vibration antinode at the transducer-line junction.

At the frequency $f_1$, since the line is a quarter-wave line, it brings infinite impedance to this very same interface which, therefore, corresponds to a minimum vibration speed called a node.

The strip 203, for its part, is always a quarter-wave strip at the frequency $f_o$ and therefore plays its pass-band widening role. On the contrary, at the frequency $f_1$, this strip no longer has a length equal to $\frac{1}{4}$th of the wavelength, and the adaptation to this frequency is therefore quite different from that obtained at the frequency $f_1$. As a result of this, the frequency band obtained around $f_o$ is smaller than the band obtained around $f_1$. However, since this frequency $f_o$ is used for DFM imaging, this kind of narrowing of the pass band is not bothersome.

As regards the impedance to be chosen for the strip 205, since this strip is transparent to the frequency $f_o$, it is necessary to choose this impedance essentially in light of the characteristics sought for the pass band around $f_1$. It has been determined that the best range is between $3.10^6$ and $20.10^6$ acoustic ohms.

Of course, the electronic equipment associated with the probe includes circuits that use frequencies, $f_o$ and $f_1$, both at transmission and at reception.

FIG. 4 shows a longitudinal cross-section of a probe according to the invention, working at 5 MHz and 2.5 MHz. It is seen that this probe has a set of transducers 201, coated with metallizations 202. These transducers are cut out of a ceramic block which is previously metallized on both sides to form the electrodes. This set of transducers is bonded to the strip 205 which is itself bonded to the backing 204. The strip 203 itself covers the transducers to which it is also bonded. It will be seen that only the block of transducers consists of individual elements while the strips 203 and 205 as well as the backing 204 are continuous. In this example, the array is linear but the invention can also be applied to arrays of other shapes, especially curved arrays.

The invention is not restricted to probes working in two frequencies where one frequency is half of the other. It also relates to probes and, generally, to acoustic transducers working in a set of distinct frequencies forming the center frequencies of separate frequency bands. For this, the number of additional adapting strips is increased so as to create the number of degrees of freedom sufficient, in the transfer function, to determine these pass bands.

Obviously, numerous modifications and variations of the present invention are possible in light of the above teachings. It is therefore to be understood that within the scope of the appended claims, the invention may be practiced otherwise than as specifically described herein.

What is claimed is:

1. A multiple-frequency acoustic transducer, especially for medical imaging, which comprises:

a piezoelectric transducer for being excited in order to emit vibrations, and at least one passive strip placed on at least one side of said piezoelectric transducer to enable said piezoelectric transducer and said at least one passive strip to resonate on at least two distinct frequencies, and a backing which acts as a support to said piezoelectric transducer wherein said backing has impedance substantially equal to zero at a first frequency and a thickness of said piezoelectric transducer and a first strip of said at least one passive strip comprises a half-wave thickness at a first resonance frequency and quarter-wave thickness at a second resonance frequency equal to half said first frequency and wherein said piezoelectric transducer comprises a segmented transducer.

2. A transducer according to claim 1 wherein a first of said at least one passive strip is placed between said piezoelectric transducer and said backing.

3. A transducer according to claim 2 which comprises a second passive strip located on an opposite side of said piezoelectric transducer with respect to said first strip, a thickness of said second passive strip being a quarter-wave thickness at a first resonance frequency and having an acoustic impedance for obtaining a band width around said first frequency.

4. A transducer according to claim 3 wherein the first frequency enables its use in mode B medical imaging and the second frequency enables its use in DFM medical imaging.

5. A transducer according to claim 4 wherein the first frequency and the second frequency are substantially equal to 5 MHz and 2.5 MHz respectively.

6. A transducer according to claim 5 wherein the acoustic impedance of said first passive strip is between $3.10^6$ and $20.10^6$ acoustic ohms.

7. A transducer according to claim 1 wherein said at least one passive strip comprises a plurality of passive strips operable in a set of distinct frequencies.

* * * * *